United States Patent [19]

Kanda et al.

[11] Patent Number: 4,926,867
[45] Date of Patent: May 22, 1990

[54] LIGHT-REFLECTING AND HEATING TYPE OXIMETER

[75] Inventors: Masahiko Kanda; Yuichi Miyagawa, both of Osaka, Japan

[73] Assignee: Sumitomo Electric Industries, Ltd., Osaka, Japan

[21] Appl. No.: 355,842

[22] Filed: May 19, 1989

Related U.S. Application Data

[63] Continuation of Ser. No. 54,889, May 27, 1987, abandoned.

[30] Foreign Application Priority Data

May 27, 1986 [JP] Japan .................................. 61-121896

[51] Int. Cl.$^5$ .................................................. A61B 5/00
[52] U.S. Cl. ..................................... 128/633; 128/640; 128/664
[58] Field of Search ............... 128/683, 640, 666, 664; 356/41

[56] References Cited

U.S. PATENT DOCUMENTS

| | | | |
|---|---|---|---|
| 3,295,515 | 1/1967 | Kahn | 128/640 |
| 3,998,550 | 12/1976 | Konishi et al. | 356/39 |
| 4,167,331 | 9/1979 | Nielsen | 356/39 |
| 4,259,963 | 4/1981 | Huch | 128/635 |
| 4,407,290 | 10/1983 | Wilber | 128/633 |
| 4,714,080 | 12/1987 | Edgar, Jr. et al. | 128/633 |
| 4,723,554 | 2/1988 | Oman et al. | 128/633 X |

FOREIGN PATENT DOCUMENTS

| | | |
|---|---|---|
| 0102816 | 3/1984 | European Pat. Off. . |
| EP0046601 | 8/1981 | Fed. Rep. of Germany . |
| 52-51785 | 4/1977 | Japan . |

OTHER PUBLICATIONS

IEEE Transactions on Biomedical Engineering, vol. BME-1, No. 12, Dec. 1984, pp. 792-800, New York, U.S., Mendelson et al., "Noninvasive Transcutaneous Monitoring of Arterial Blood Gases".

Primary Examiner—William E. Wayner
Attorney, Agent, or Firm—Cushman, Darby & Cushman

[57] ABSTRACT

A light-reflecting and heating type oximeter designed to measure non-invasively oxygen saturation in blood contained in a part of a living body by using an optical sensor. The optical sensor has a light-emitting section for emitting measuring light beams having at least two different wavelengths and a light-receiving section for receiving the measuring light beams activated by and reflected from the measuring part of the living body, and a heating means whose heating temperature is controllable is provided around the light-emitting and -receiving sections. The light receiving section and light emitting section are arranged in a particular positional relationship on a flat surface of the optical sensor housing to obtain accurate measurements. The arrangement enables measurement of oxygen saturation in any part of a living body including those in which blood vessels are distributed close to the body surface, such as finger tips, ears and the flat part of a newborn's foot.

8 Claims; 3 Drawing Sheets

LIGHT-REFLECTING AND HEATING TYPE OXIMETER

This is a continuation of application Ser. No. 54,889, filed May 27, 1987, which was abandoned upon the filing hereof.

BACKGROUND OF THE INVENTION

1. Field of the Invention

The present invention relates to a light-reflecting and heating type oximeter designed to non-invasively measure oxygen saturation in the blood contained in a part of a living body by using an optical sensor.

2. Description of the Prior Art

One type of conventional non-invasive oximeter is designed to continuously and non-invasively measure oxygen saturation in the blood contained in a part of a living body by using an optical sensor. This type of optical oximeter utilizes the relative difference between the light absorption coefficient of Hb (deoxygenated hemoglobin) and that of $HbO_2$ (oxygenated hemoglobin). More specifically, two light beams having different wavelength are directed to and transmitted through a part (finger, ear or the like) of a living body. The two different kinds of transmitted light are received by means of photosensors and the oxygen saturation in the blood contained in the part being measured is obtained on the basis of the ratio of two light absorption coefficients that represent the extent of the absorption of said two different kinds of light in the part of the living body being measured. Examples of this type of prior art include pulsation type oximeters such as those disclosed in U.S. Pat. No. 3,998,550 (Japanese Patent Publication No. 57-25217), E.P. application No. 83304939.8 (E.P. Publication No. 0102816; Japanese Patent Public Disclosure No. 59-16,445), U.S. Pat. No. 4,167,331 (Japanese Patent Public Disclosure No. 53-88778) and U.S. Pat. No. 4,407,290 (Japanese Patent Domestic Announcement No. 58-500432. According to these disclosed techniques, two light beams having different wavelength are directed to and transmitted through a part of a living body as described above. In these prior art oximeters, comparison is made between one state wherein pulsating arterial blood has flowed into blood vessel in the part of the living body being measured and consequently the amount of blood therein has increased and another state wherein the pulsating arterial blood has flowed out of the relevant part and the amount of blood has accordingly decreased, and information regarding light absorption by blood alone is obtained on the basis of the difference between the two states, that is, the pulsating component.

However, the above-described method has the disadvantage that, since measurement is effected using light which has been transmitted through a part of a living body, measurable parts are undesirably limited to parts with a relatively thin layer of tissue such as ears, fingers and the flat part of a newborn's foot. Therefore, it is impossible to measure arterial oxygen saturation in those parts of living bodies which do not allow measuring light beams to be sufficiently transmitted.

To overcome this problem, Japanese Patent Public Disclosure No. 52-51785 proposes a light-reflecting type oximeter which utilizes light reflected from a body part being measured so that all parts of living bodies can be measured. However, this light-reflecting type oximeter still suffers from the following disadvantage. Since measurement is effected on the premise that light is partially absorbed by the part of a living body being measured, the parts which are measurable are in practice limited to those in which blood vessels are distributed close to the body surface, such as fingers and ears. Therefore, it is difficult to detect pulsating components in other parts of living bodies, apart from fingers and ears, so that the oxygen saturation therein cannot be measured.

SUMMARY OF THE INVENTION

In view of these circumstances, it is a primary object of the present invention to provide a light-reflecting and heating type oximeter which is so designed that a part of a living body to be measured is heated by a heating means so as to bring and keep the blood vessel network in the part being measured in an arterialized state in order to increase the amount of blood flowing therein, thereby enabling detection of a relatively large pulsating component and, hence, highly sensitive measurement of oxygen saturation, and thus permitting measurement of oxygen saturation in all parts of living bodies including those in which blood vessels are distributed close to the body surface, such as fingers and ears.

To this end, the present invention provides a light-reflecting and heating oximeter designed to measure non-invasively oxygen saturation in the blood contained in a part of a living body by using an optical sensor, wherein the optical sensor has a light-emitting section that emits measuring light beams having at least two different wavelengths and a light-receiving section for receiving the measuring light scattered and reflected from the part of the living body being measured and a heating means whose heating temperature is controllable is provided around the light-emitting and -receiving sections.

More specifically, when the skin is heated (to more than 42° C.), arterioles in the blood vessel network spreading in the shallow layer within the dermis are thermally stimulated, and their smooth muscles respond to the stimulation to expand the inner diameters of the arterioles, resulting in a lowering in resistance to the blood flow. In consequence, and this causes capillaries to be expanded to increase the amount of blood flowing therethrough.

Normally, when blood passes through capillaries, oxygen is consumed by the tissue, and the conversion from arterial blood into venous blood is thus carried out. In contrast, when the capillaries are in a heated state as described above, the amount of blood flowing therethrough is relatively large and the velocity of blood flow is relatively high. Therefore, blood which is still in an arterial blood state flows into the venules.

Accordingly, directly under the heated part and its periphery, almost all the blood flowing through all the blood vessels (arterioles, capillaries and venules) in the dermal shallow layer is kept in an arterialized state.

The size of the pulsating component is proportional to the amount of arterial blood flowing through the part being measured. Therefore, it is possible to obtain a relatively large pulsating component for each measuring wavelength in any part of a living body including those in which blood vessels are distributed close to the body surface, such as fingers and ears. Thus, oxygen saturation can advantageously be measured in any part of a living body.

BRIEF DESCRIPTION OF THE DRAWINGS

The above and other objects, features and advantages of the present invention will become more apparent from the following description of the preferred embodiment thereof, taken in conjunction with the accompanying drawings in which like reference numerals denote like elements or portions, and in which.

DESCRIPTION OF THE PREFERRED EMBODIMENT

One preferred embodiment of the present invention will be described hereinunder in detail with reference to the accompanying drawings.

Figure 1A:
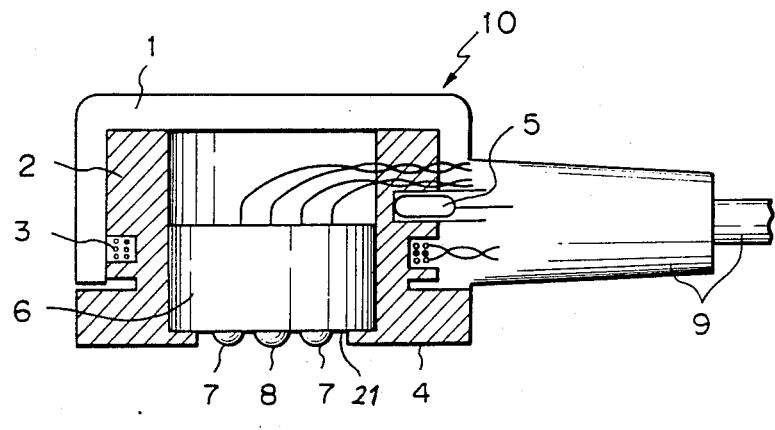
FIG. 1A is a longitudinal sectional view of a sensor section of one embodiment of the light-reflecting and heating type oximeter according to the present invention.
Figure 1B:
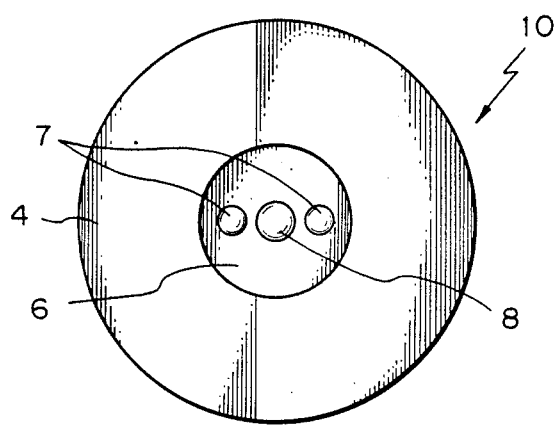
FIG. 1B is a bottom view of the sensor section shown in FIG. 1A.

FIGS. 1A and 1B show in combination a sensor section of one embodiment of the light-reflecting and heating type oximeter according to the present invention.

In the drawings, the reference numeral 1 denotes a sensor cover, 2 a heating body made from a heat conductive material (e.g., a metal), and 3 a heater defined by, for example, a nichrome wire. The heating body 2 is heated by means of the heater 3 in order to heat a part of a living body to be measured through a contact surface 4. The temperature of the heating body 2 is measured by means of a thermistor 5, and the supply of electric current to the heater 3 is controlled so that the temperature of the heating body 2 is maintained at a constant level. As illustrated, an optical sensor 6 is incorporated in the heating body 2. The optical sensor 6 has its own housing that has a flat surface end 21 to which are attached two light-emitting elements 7 which respectively emit two different kinds of measuring light having wavelengths which are different from each other and one light-receiving element 8. Both light-emitting elements 7, light-receiving element 8, and end part 2A of contact surface 4 protrude a substantially equal amount from flat surface end 21, as shown in FIG. 1A. Light which is emitted from each of the light-emitting elements 7 is applied to the inside of a living body under test. The measuring light is partially absorbed by the tissue inside the living body and the remaining light which is scattered and reflected from the living tissue is detected by means of the light-receiving element 8. Light receiving element 8 is arranged on flat surface end 21 so that it is between light emitting elements 7.

Figure 2:
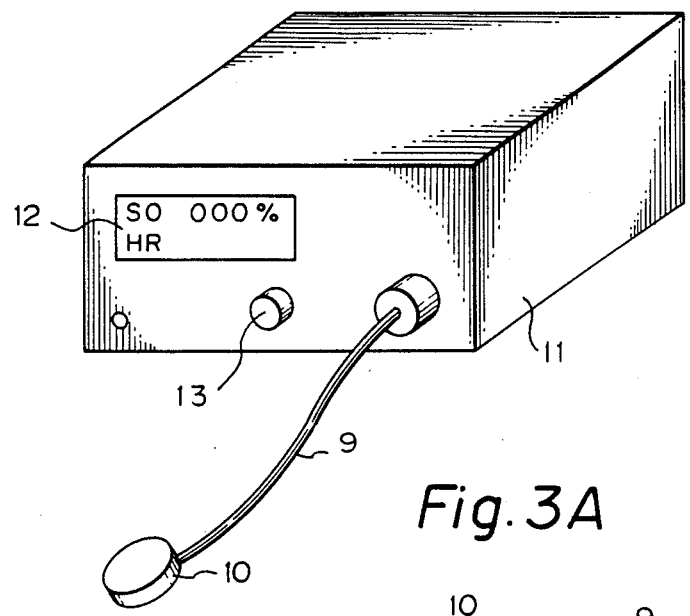
FIG. 2 is a perspective view of one embodiment of the light-reflecting and heating type oximeter according to the present invention.

Various kinds of wire, that is, wires used to drive the light-emitting elements 7, wires for supplying electric current to the heater 3 and signal wires for the light-receiving element 8 and the thermistor 5, are put together in the form of a lead wire 9 which is led from the sensor section 10 and connected to the oximeter 11 as shown in FIG. 2. The oximeter 11 processes a pulsating component signal relating to absorbance for each measuring wavelength which is detected in the sensor section 10 and displays the heart rate HR and the oxygen saturation $SO_2$ on a display section 12. The oximeter 11 is provided with a temperature setting knob 13 in order to enable control of the temperature of the heating body 2 in the sensor section 10.

Figure 3A:
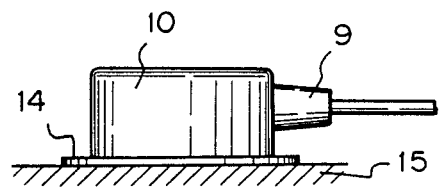
FIG. 3A is a side view showing the way in which the sensor section is stuck to a part of a living body.
Figure 3B:
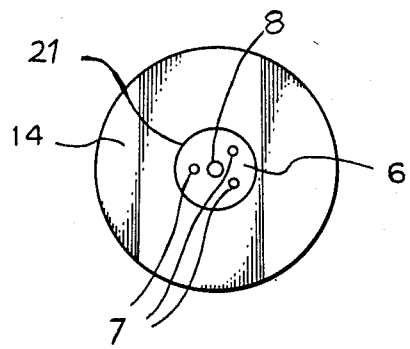
FIG. 3B is a bottom view of the sensor section.
Figure 4A:
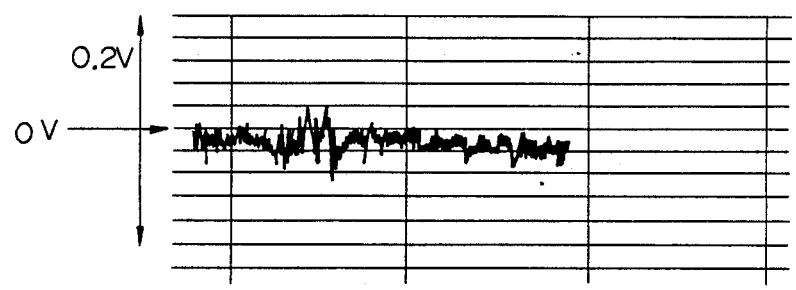
FIG. 4A is a graph showing an example of measurement of the pulsating component at an arbitrary wavelength obtained using a conventional light-reflecting (and non-heating) type oximeter.
Figure 4B:
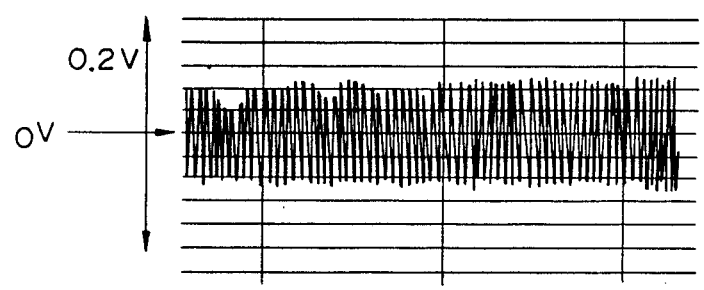
FIG. 4B is a graph showing a similar example of measurement carried out using the light-reflecting and heating type oximeter according to the present invention.

To measure oxygen saturation in a part of a living body using the above-described light-reflecting and heating type oximeter 11, the sensor section 10 is stuck to a part 15 of the living body by using a ring-shaped piece of double-coated adhesive tape 14 as shown in FIGS. 3A and 3B. Next, temperature setting is effected by actuating the temperature setting knob 13 so that the temperature of the heating body 2 is maintained within a range of from 42° to 44° C. Then, the body surface of the part 15 is heated through the contact surface 4 of the heating body 2. Thus, arterioles in the blood vessel network spread through the shallow layer within the dermis are thermally stimulated, and their smooth muscles respond to the stimulation to expand the inner diameters of the arterioles resulting in a lowering in resistance to the blood flow. In consequence, the amount of blood flowing through the arterioles increases, and this causes the capillaries to be expanded to increase the amount of blood flowing therethrough. Accordingly, the output of the light-receiving element 8 reaches a sufficiently high level to accurately detect the pulsating component, as shown in FIG. 4B. Whereas, when the measuring part 15 is not heated during the measurement, the output of the light-receiving element 8 is insufficient to accurately detect the pulsating component as shown in FIG. 4A. Thus, oxygen saturation can be obtained by detecting this pulsating component with respect to each of the two different kinds of measuring light respectively emitted from the light-emitting elements 7 and having wavelengths that are different from each other, through the known computational equation employed in conventional oximeters.

It should be noted that, although this embodiment employs two light-emitting elements 7 which emit two different kinds of measuring light beams having wavelengths that are different from each other, oxygen saturation may also be obtained by employing three or more light-emitting elements which emit three or more different kinds of measuring light beams having wavelengths that are different from each other and by using a computational equation which is different from the above-described one. As shown in FIG. 3B, three light emitting elements 7 are arranged concentrically around light-receiving element 8 on flat surface end 21.

As has been described above, the present invention enables measurement of oxygen saturation in any part of a living body, whereas with the prior art the parts which are measurable are limited to those in which blood vessels are distributed close to the body surface.

Although the present invention has been described through specific terms, it should be noted here that the described embodiment is not necessarily exclusive and various changes and modifications may be imparted thereto without departing from the scope of the invention which is limited solely by the appended claims.

What is claimed is:

1. An oximeter sensor for non-invasively measuring oxygen saturation of blood contained within a part of a living body comprising:
   optical sensor means for measuring oxygen blood saturation, said optical sensor means including:
   a housing containing a flat surface end adaptable to face said body part,
   means for emitting measuring light having at least two different wavelengths protruding from said flat surface end, said light emitting means including at least two light emitting elements that emit different wavelengths of measuring light, and
   means for receiving said measuring light protruding from said flat surface end between said at least two light emitting elements; and
   means for controllably heating said body part containing a contact surface adaptable to be placed on said body and disposed around and protruding from said flat surface and of said housing substantially the same amount as said light emitting means and said light receiving means.

2. An oximeter sensor according to claim 1 wherein said heating means comprises a heating body and a heater for heating said heating body.

3. An oximeter sensor according to claim 2, wherein said heating body surrounds said optical sensor.

4. An oximeter sensor according to claim 2, wherein said heating body further includes temperature measuring means for measuring the temperature of said heating body.

5. An oximeter sensor according to claim 4, wherein said temperature measuring means is a thermistor.

6. An oximeter sensor according to claim 2, wherein said heating body is stuck to the part of the living body being measured using double-coated adhesive tape.

7. An oximeter sensor according to claim 1 wherein said light emitting means includes three light emitting elements disposed on said flat surface end and arranged concentrically around said light receiving means.

8. An oximeter sensor according to claim 1 wherein said heating means heats skin on said body part to at least 42° C.

* * * * *